United States Patent

Brisson et al.

Patent Number: 5,329,928
Date of Patent: Jul. 19, 1994

[54] REFLECTED SHOCKWAVE SHIELDING DEVICE

[75] Inventors: A. Glen Brisson, Kildeer; Exequiel D. Cruz, Arlington Heights; Dianne L. Vickers, Cary, all of Ill.

[73] Assignee: Bantum Tripter Joint Venture, Columbus, Ohio

[21] Appl. No.: 106,855

[22] Filed: Aug. 16, 1993

[51] Int. Cl.$^5$ .............................................. A61B 17/22
[52] U.S. Cl. ...................................... 128/660.03; 601/3
[58] Field of Search .......... 128/24 AA, 24 EL, 660.03

[56] References Cited

U.S. PATENT DOCUMENTS

| | | |
|---|---|---|
| 5,060,634 | 10/1991 | Beukan et al. ............... 128/24 EL |
| 5,209,222 | 5/1993 | Viebach et al. ............... 128/24 EL |
| 5,228,447 | 7/1993 | Harder et al. ............... 128/24 EL |

Primary Examiner—Ruth S. Smith
Attorney, Agent, or Firm—Robert M. Wolters

[57] ABSTRACT

An extracorporeal lithotripter has an ultrasound transducer mounted within the lithotripter reflector. The reflector and transducer are oriented downwardly, and a housing surrounds the transducer to protect the transducer from shockwaves generated within the reflector at the first focus point thereof. The housing opens downwardly, and a sleeve encircles the lower portion of the housing and extends below the housing. A conduit is connected to the sleeve to provide pressure less than atmospheric in said sleeve to effect filling of said sleeve with water for operation of the ultrasound transducer. The conduit alternatively and selectively effects filling of the sleeve with gas to protect against reflected shockwaves from below that might otherwise damage the transducer.

7 Claims, 1 Drawing Sheet

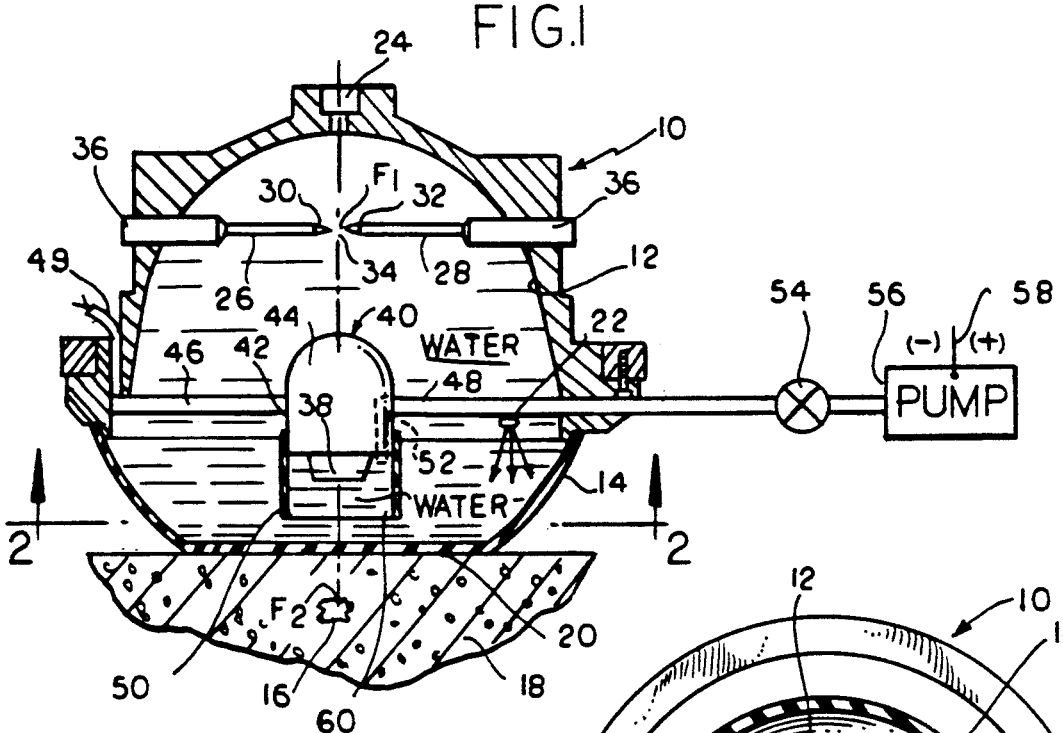
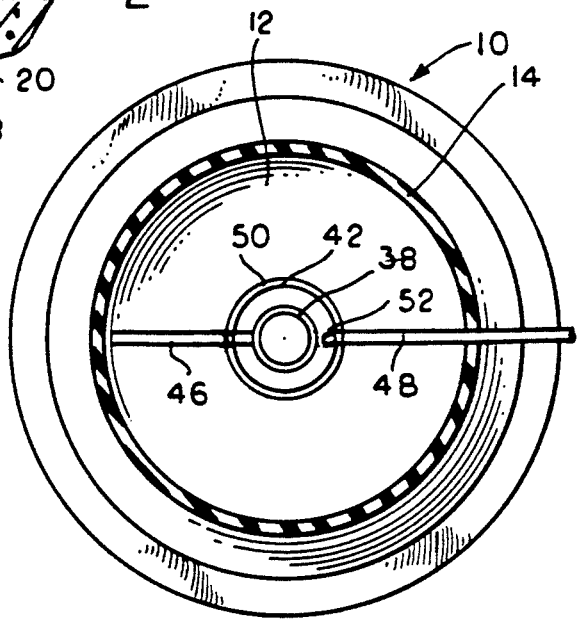
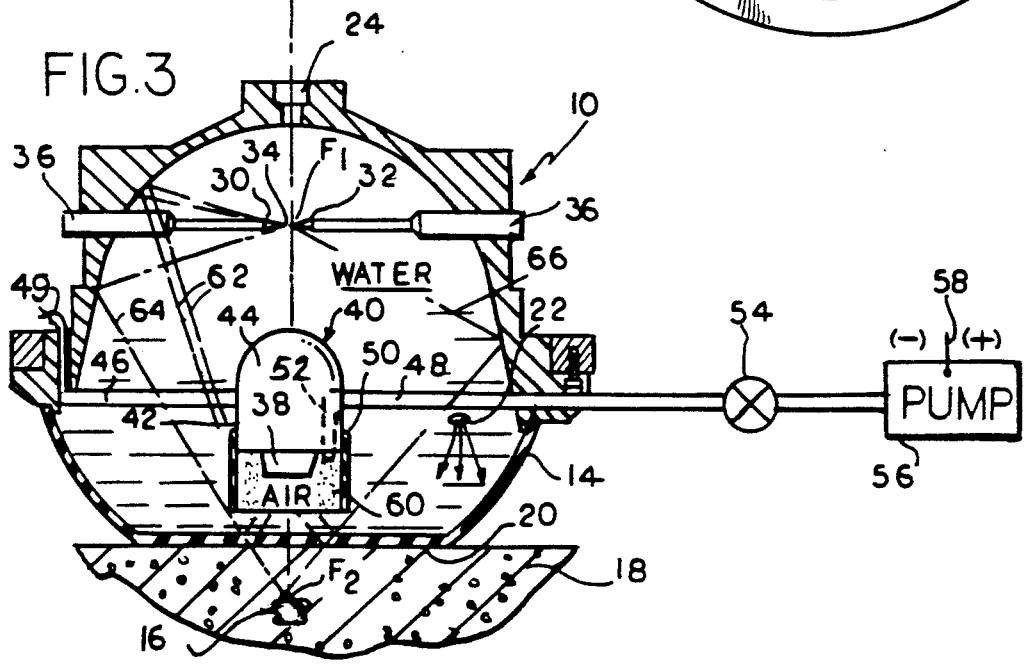

REFLECTED SHOCKWAVE SHIELDING DEVICE

BACKGROUND OF THE INVENTION

Most extracorporeal lithotripters utilize x-rays and/or ultrasound devices for aiming the reflector of the lithotripter to place the second focus point directly on the kidney stone that is to be destroyed. In our copending application Ser. No. 07/856,373, filed Mar. 23, 1992 with the title ULTRASOUND TRANSDUCER SHIELDING now U.S. Pat. No. 5,240,002) we have disclosed an extracorporeal lithotripter in which aiming is accomplished by way an ultrasound transducer mounted within the reflector in fixed relation thereto. We have provided a heavy metallic shield surrounding the transducer that protects the transducer from direct shockwaves generated by the spark gap in the reflector. Further study has indicated that there may be some shockwaves reflected by the interface between the reflector diaphragm and the human body which could bounce up against the ultrasound transducer to cause damage thereto.

OBJECTS AND SUMMARY OF THE PRESENT INVENTION

It is an object of the present invention to protect an ultrasound transducer in the reflector in an extracorporeal lithotripter from damage by reflected shockwaves.

Furthermore, it is an object of the present invention to protect such an ultrasound transducer at very low, nearly nominal cost.

In carrying out the foregoing objects, we rely on the fact that the shockwaves are transmitted very well through an aqueous medium, but are substantially not transmitted at all through air. Our previously identified copending application 07/856,373 utilizes a substantially cylindrical metallic shield with a hemispherical top. The lower portion of the shield is terminated short of the lowermost portion of the ultrasound transducer. In the present invention we provide a silicone rubber sleeve encircling the lower portion of the metallic shield and depending some distance therebelow. We provide a conduit which alternatively provides air under moderate pressure to expel water from the sleeve, or to provide air at negative pressure to cause water in the reflector to fill the sleeve. During aiming of the reflector the sleeve is full of water, and the ultrasound waves are readily transmitted to and from the transducer as if the sleeve were actually not there. However, once aiming has been effected, and shockwave generation is to begin, air is pumped into the sleeve to exclude water therefrom, and shockwaves will not pass through the air to the ultrasound transducer.

BRIEF DESCRIPTION OF THE DRAWINGS

The present invention will best be understood with reference to the ensuing specification when taken in connection with the accompanying drawings wherein:

FIG. 1 is a longitudinal section through the lithotripter reflector and associated parts;

FIG. 2 is an upwardly looking horizontal sectional view as taken substantially along the line 2—2 in FIG. 1; and FIG. 3 is a view similar to FIG. 1, but with the sleeve full of air, rather than water.

DETAILED DISCLOSURE OF THE ILLUSTRATED EMBODIMENT OF THE INVENTION

Referring first to FIG. 1, a lithotripter reflector assembly 10 has an ellipsoidal reflector surface 12. The reflector is aimed downwardly, and has an open lower end closed by a rubber diaphragm 14 suitably secured to the lower end of the reflector. The reflector has a first focus point F1 within the reflector and relatively toward the top or apex thereof. There is a second focus point F2 which is disposed beyond the diaphragm 14, and which is intended for superposition on a kidney stone 16 within the body of a patient, a fragment of which is shown at 18. The diaphragm flattens as indicated at 20 to a greater or lesser extent to conform to the body, and to position the reflector at a proper distance from the kidney stone 16 so that the second focus point F2 lies on the kidney stone. An opening 22 in the reflector provides for entrance of water, and an opening 24 at the apex of the reflector provides for the exit of water. The plumbing connections are not pertinent to the present invention, and are not further shown.

A pair of electrodes 26 and 28 extend into the reflector in alignment with one another. The electrodes have spaced metallic tips 30 and 32, respectively, providing between them a gap 34 coincident with the first focus point F1. A high voltage spark across the gap causes some of the water in the reflector to be flashed into steam and sets up a shockwave that is reflected by the walls of the reflecting surface or reflector 12. The electrodes 26 and 28 are mainly made of brass, and each is covered by an insulating silicone rubber sleeve. Each electrode, including the sleeve thereon, is suitably mounted by plastic insulating material 36 in the metallic reflector. The specific mounting structure and the electrical connection thereto to produce periodic sparks across the gap are not particularly important in the present invention, and are not shown further. As will be understood, external electrical apparatus is provided for producing pulses of electrical energy that are connected to the electrodes to produce the requisite sparks. An ultrasound transducer 38 is mounted within a massive brass shield 40. The shield is mainly cylindrical, having a cylindrical wall 42. The uppermost portion comprises a hemisphere 44. The shield 40 is mounted by a pair of diametrically disposed arms 46 and 48 extending to the sidewalls of the reflector assembly 10. The arm 46 is hollow, and carries wiring 49 leading to the ultrasound transducer 38. Further details of the mounting of the shield and of the transducer need not be described here, but are shown in detail in our aforesaid application Ser. No. 07/856,373.

What is important to the present invention is a silicone rubber sleeve 50 surrounding the cylindrical wall 42 of the shield 40 and depending therefrom beyond the lowermost limits of the ultrasound transducer 38. The sleeve 50 may be secured to the cylindrical wall 42 simply by its own elasticity, or it may be surrounding by a band in the nature of a hose clamp or the like, or any other suitable structure. The supporting arm 48 also is hollow, and has a vertical portion 52 extending below the bottom edge of the shield 40, and into the space within the silicone rubber sleeve 50. The arm 48 is connected exteriorly of the reflector housing assembly 10 to a valve 54 and an air pump 56, having a control 58 so that the pump may supply either positive or negative air pressure to the hollow tube 48, and hence to the space 60 within the silicone sleeve 50.

The underside of the reflector body, etc. is shown in FIG. 2. However, the electrode structure has been omitted from FIG. 2 to avoid unnecessarily complicating the drawing. The points of primary interest in all of the figures comprise the silicone rubber sleeve 50 and the piping 48, 52 associated therewith for introducing air under positive or slight negative pressure into the space 60 within the silicone sleeve. It might be noted that silicone is used as a very satisfactory material for the sleeve, but that other materials might be satisfactory.

Operation of the present invention will best be understood with comparison between FIGS. 1 and 3. In FIG. 1 the entire reflector, and also the space 60 within the sleeve are full of water. In this condition the ultrasound transducer 38 is used with external connections including a monitor screen to permit localization of the reflector so that the second focus point F2 lies on the kidney stone 16. The ultrasound waves from the transducer 38 transmit very nicely through the water in the reflector, and in the sleeve space 60, and also through the rubber diaphragm 20, and the human body, which is more than 80 percent water. However, when it is desired to produce the shockwaves to fracture the kidney stone, the valve 54 and the control 58 are operated to produce a sufficient positive pressure to introduce air into the space 60, and to displace water therefrom. Various reflective waves are illustrated.

For example-two shockwaves 62 eminating from the spark gap 34 at the first focus point F1 engage the silicone sleeve 50, but since the air now in the space 60 will not transmit the shockwaves, the waves either are reflected away from the sleeve, or are simply dissipated in the water within the reflector. Another shockwave representation 64 passes below the sleeve 60 and engages the kidney stone 16 to fracture it as is true also of shockwave 66. However, most importantly, part of the energy of waves such as 64 and 66 is reflected up to the space 60, which, if it were full of water, would carry such energy on to the transducer 38, and might cause damage thereto. As will be understood the interface between the water in the reflector and diaphragm and the diaphragm and body forms a reflective surface. However, the wave 66 upon reflecting up from this interface engages the air within the space 60, and the air will not transmit the shockwave. The shockwave may to some extent be reflected by the interface between the water and the air, but mostly simply dissipates in the water upon reaching that interface.

Thus, for the very minimal cost of the silicone sleeve 50, and the slight added cost of the piping to supply positive or negative pressure air to the space within the sleeve, we have been able to provide protection for the transducer 38 against shockwaves that might otherwise be reflected up from the water/diaphragm/body to cause damage to the transducer. It will also be understood that the depending portion of the diaphragm between the water in the reflector and diaphragm, and the air outside of the diaphragm forms a reasonably reflective interface, and any shockwaves reflected therefrom are prevented by the air space within the silicone sleeve from reaching the ultrasound transducer 38.

In the present system, due to the depending nature of the diaphragm and the water restrained thereby, a pressure somewhat below atmospheric is maintained on the water. At best, for the water completely to fill the space 60 within the silicone rubber sleeve, it is necessary for the pump 56 to develop a slight pressure below atmospheric in order completely to fill the space 60 with water. Our water system and the maintenance of pressure therein below atmospheric pressure may be seen in our prior copending application Ser. No. 07/856,352, filed Mar. 23, 1992 (now allowed).

Reference has been made to filling the space 60 with air as illustrated in FIG. 3. Air is used in a generic sense, as other gases would be effective in blocking shockwaves. However, air is readily available and satisfactory. However, it is to be understood that in the broadest sense the space 60 could be filled with some other gas or mixture of gases, rather than air.

The specific example of the invention as heretofore shown and described is for illustrative purposes only. Various changes may occur to those skilled in the art, and will be understood as forming a part of the invention, insofar as they fall within the scope of the appended claims.

The invention is claimed as follows:

1. In an extracorporeal lithotripter comprising a truncated ellipsoidal reflector open at one end, said one end being downwardly directed substantially toward the surface of the earth, a rubber diaphragm closing said open end; said reflector having a first focus point within said reflector and a second focus point outside said reflector and beyond said diaphragm, said reflector having an axis of rotation which passes through both of said focus points, said reflector and said diaphragm comprising a volume filled with water, a pair of electrodes in said reflector and having ends in spaced relation providing a spark gap at said first focus point, an electrical spark between said electrodes across said gap producing a shockwave focused by said reflector on said second focus point, an ultrasound transducer within said reflector and aimed toward said second focus point, and a housing for said transducer, said housing being supported from said reflector adjacent said reflector open end and having a rounded upper end disposed toward said spark gap to deflect shockwaves, said housing having an open end and a bore opening at said housing end toward said second focus point, said transducer being mounted in said bore and aimed downwardly thereof, the improvement comprising means extending downwardly from said housing toward said diaphragm and defining a downwardly opening space, means opening into said space and selectively operable to effect filling of said space with water or a gas, water in said space conducting soundwaves to and from said transducer, and gas being nonconductive of shockwaves to guard said transducer against reflected shockwaves from below.

2. The combination as set forth in claim 1 wherein the means defining said space is cylindrical.

3. The combination as set forth in claim 2 wherein the means defining said space is resilient.

4. The combination as set forth in claim 2 wherein the means defining said space comprises a sleeve encircling said transducer housing open end and extending downwardly therefrom.

5. The combination as set forth in claim 2 wherein the means for effecting filling of said space includes means for pumping gas into said space.

6. The combination as set forth in claim 5 wherein said pumping means capable of connecting a pressure less than atmospheric to said space to permit entry of water therein to.

7. The combination as set forth in claim 1 wherein the means defining said space is resilient.

* * * * *